(12) United States Patent
Tenbrink et al.

(10) Patent No.: US 6,855,709 B2
(45) Date of Patent: Feb. 15, 2005

(54) PYRIDYL SULFONE DERIVATIVES

(75) Inventors: Ruth E. Tenbrink, Kalamazoo, MI (US); Steven W. Kortum, Kalamazoo, MI (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 0 days.

(21) Appl. No.: 10/371,391

(22) Filed: Feb. 20, 2003

(65) Prior Publication Data

US 2003/0186968 A1 Oct. 2, 2003

Related U.S. Application Data

(60) Provisional application No. 60/359,174, filed on Feb. 22, 2002.

(51) Int. Cl.$^7$ .................. C07D 243/08; C07D 401/00; A61K 31/55; A61K 31/495; A61P 25/22
(52) U.S. Cl. .................. 514/218; 514/253.01; 540/575; 544/360
(58) Field of Search ............................ 514/218, 253.01; 540/575; 544/360

(56) References Cited

U.S. PATENT DOCUMENTS 5,770,613 A 6/1998 Gaeta et al. ................ 514/332

FOREIGN PATENT DOCUMENTS

| EP | 0 156 433 | 10/1985 | | |
|---|---|---|---|---|
| EP | 0 815 861 A | 1/1998 | | |
| JP | 61-280474 | 11/1986 | | |
| JP | 11-72377 | 7/1989 | | |
| JP | 10182636 | * | 7/1998 | ......... C07D/403/04 |
| WO | 98-24782 | 8/1998 | | |
| WO | WO 99 37623 A | 7/1999 | | |
| WO | WO 02/40456 A | 5/2002 | | |

OTHER PUBLICATIONS

Gavezzoti (Acc. Chem. Res. 1994, 27, 309–314).*

* cited by examiner

*Primary Examiner*—Bruck Kifle
(74) *Attorney, Agent, or Firm*—Mary J. Hosley

(57) ABSTRACT

The invention provides compounds of the formula

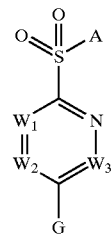

and methods of using those compounds for treating a disease or condition in a mammal wherein a 5-HT receptor, such as a 5-HT$_6$ receptor, is implicated and modulation of a 5-HT function is desired, wherein A, G and W$_1$–W$_3$ are defined as herein.

25 Claims, No Drawings

PYRIDYL SULFONE DERIVATIVES

CROSS-REFERENCE TO RELATED APPLICATION

This application claims the benefit of U.S. provisional application Ser. No. 60/359,174, filed Feb. 22, 2002, under 35 USC 119(e)(i), which is incorporated herein by reference.

FIELD OF THE INVENTION

The present invention relates to novel pyridylsulfone derivatives, and more specifically, relates to pyridylsulfone compounds of formulae I and II described herein below. These compounds are 5-HT receptor ligands and are useful for treating diseases wherein modulation of 5-HT activity is desired.

BACKGROUND OF THE INVENTION

Serotonin has been implicated in a number of diseases and conditions that originate in the central nervous system. These include diseases and conditions related to sleeping, eating, perceiving pain, controlling body temperature, controlling blood pressure, depression, anxiety, schizophrenia, and other bodily states. Serotonin also plays an important role in peripheral systems, such as the gastrointestinal system, where it has been found to mediate a variety of contractile, secretory, and electrophysiologic effects.

As a result of the broad distribution of serotonin within the body, there is a tremendous interest in drugs that affect serotonergic systems. In particular, agonists, partial agonists and antagonists are of interest for the treatment of a wide range of disorders, including anxiety, depression, hypertension, migraine, obesity, compulsive disorders, schizophrenia, autism, neurodegenerative disorders (e.g. Alzheimer's disease, Parkinsonism, and Huntington's chorea), and chemotherapy-induced vomiting.

The major classes of serotonin receptors ($5$-$HT_{1-7}$) contain fourteen to eighteen separate receptors that have been formally classified. See Glennon, et al., Neuroscience and Behavioral Reviews, 1990, 14, 35; and D. Hoyer, et al. Pharmacol. Rev. 1994, 46, 157–203.

There is currently a need for pharmaceutical agents that are useful to treat diseases and conditions that are associated with 5-HT receptors. In particular, there is a need for agents that can selectively bind to individual receptor sub-types (e.g. receptor-specific agonists or antagonists); such agents would be useful as pharmaceutical agents, or would be useful to facilitate the study of the 5-HT receptor family, or to aid in the identification of other compounds that selectively bind to the specific 5-HT receptors.

For example, The $5$-$HT_6$ receptor was identified in 1993 (Monsma et al. Mol. Pharmacol. 1993, 43, 320–327 and Ruat, M. et al. Biochem. Biophys. Res. Com. 1993, 193, 269–276). Several antidepressants and atypical antipsychotics bind to the $5$-$HT_6$ receptor with high affinity and this binding may be a factor in their profile of activities (Roth et al. J. Pharm. Exp. Therapeut. 1994, 268, 1403–1410; Sleight et al. Exp. Opin. Ther. Patents 1998, 8, 1217–1224; Bourson et al. Brit. J. Pharm. 1998, 125, 1562–1566; Boess et al. Mol. Pharmacol. 1998, 54, 577–583; Sleight et al. Brit. J. Pharmacol. 1998, 124, 556–562). In addition, the $5$-$HT_6$ receptor has been linked to generalized stress and anxiety states (Yoshioka et al. Life Sciences 1998, 17/18, 1473–1477). Together these studies and observations suggest that compounds that antagonize the $5$-$HT_6$ receptor will be useful in treating disorders of the central nervous system.

INFORMATION DISCLOSURE

U.S. Pat. No. 5,770,613 discloses pyridines useful for the treatment of cancer and for contraceptive use.

JP 61-280474 discloses alkyl, alkenyl and aryl sulfonyl pyridine used as intermediates for drugs; agrochemicals, surfactants, etc.

EP 0 156 433 discloses pyridazinamines useful as antiviral agents.

JP 11-72377 discloses monocyanopyrazines which are useful for agrochemicals and pharmaceuticals.

WO 98/24782 discloses pyrimidine compounds useful for the prophylaxis and treatment of TNF-alpha, IL-1beta, IL-6 and/or IL-8 mediated diseases and other diseases such as pain and diabetes.

SUMMARY OF THE INVENTION

In one aspect, the invention features compounds of formula I:

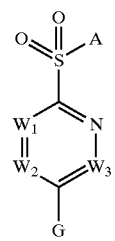

wherein $W_1$–$W_3$ are —C(R) or N with the proviso that no more than one of $W_1$–$W_3$ are nitrogen, and further provided that when $W_2$ is N that $W_3$ is not —C(CN);

A is a five- or six-membered monocyclic aromatic ring; a eight- or ten-membered fused aromatic ring system, the five- or six-membered monocyclic aromatic ring and the eight- or ten-membered fused aromatic ring system each optionally containing up to three heteroatoms (O, N, S); or a nine-membered fused aromatic ring system containing one to three heteroatoms (O, N, S), each of the five- or six-membered monocyclic aromatic ring and the eight- to ten-membered fused aromatic ring systems being optionally substituted with 1–4 of R;

Each R is independently selected from H, halo, alkyl, cycloalkyl, substituted alkyl, —OH, alkoxy, substituted alkoxy, —SH, —S-alkyl, —S-substituted alkyl, —CN, —$NO_2$, —$NR_1R_2$, —$NR_1SO_2$-alkyl, —$NR_1SO_2$-aryl, —$COOR_3$, —$CONR_1R_2$, —$SO_2NR_1R_2$, —$SO_2$-alkyl, het, substituted het, aryl and substituted aryl;

G is

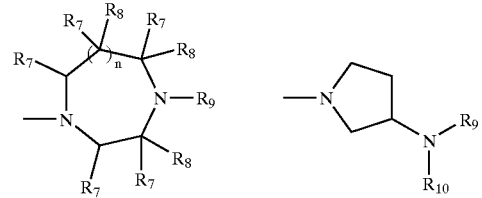

-continued

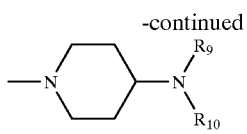

Each $R_1$ and $R_2$ is independently H, alkyl, cycloalkyl, substituted alkyl, aryl, het, substituted aryl, and substituted het, or $R_1$ and $R_2$ when taken together, along with the atom to which they are bound, form a five, six, or seven-membered ring which contains 1–3 heteroatoms selected from N, O, or S;

Each $R_3$ is independently H, alkyl, cycloalkyl, or substituted alkyl;

Each $R_7$ is independently H, or alkyl, or oxo provided that $R_8$ is absent when the oxo moiety is bound to the same carbon;

Each $R_8$ is independently H or alkyl;

Each $R_9$ and $R_{10}$ is independently H, alkyl, or substituted alkyl; and n is 0–1.

Generally, compounds of the present invention are 5-HT ligands. In particular, they can selectively bind to the 5-HT$_6$ receptor (e.g. receptor-specific agonists or antagonists). Thus, they are useful for treating diseases wherein modulation of 5-HT activity, specifically 5-HT$_6$ activity, is desired. Therefore, the compounds of this invention are useful for the treatment of diseases or disorders of the central nervous system. More specifically, for the treatment of psychosis, paraphrenia, psychotic depression, mania, schizophrenia, schizophreniform disorders, anxiety, migraine headache, drug addiction, convulsive disorders, personality disorders, post-traumatic stress syndrome, alcoholism, panic attacks, obsessive-compulsive disorders, and sleep disorders. The compounds of this invention are also useful to treat psychotic, affective, vegetative, and psychomotor symptoms of schizophrenia and the extrapyramidal motor side effects of other antipsychotic drugs. This last action will allow higher doses of antipsychotics to be used and thus greater antipsychotic efficacy to be obtained as a result of a reduction in side effects. The compounds of this invention are also useful in the modulation of eating behavior and thus are useful in treating excess weight and associated morbidity and mortality.

The present invention further provides a method for treating diseases or disorders of the central nervous system comprising administering a therapeutically effective amount of a compound of formula I or II, or a pharmaceutically acceptable salt thereof to the mammal. The term treating includes prophylactic treatment. In particular, compounds of formula I or II are useful in treating depression, schizophrenia, schizophreniform disorder, and schizoaffective disorder. In some embodiments compounds of formula I or II may have activity against other diseases or disorders including, but are not limited to, the following: obesity, delusional disorder, a stress related disease (e.g. general anxiety disorder), panic disorder, a phobia, obsessive compulsive disorder, post-traumatic-stress syndrome, immune system depression, a stress induced problem with the urinary, gastrointestinal or cardiovascular system (e.g., stress incontinence), neurodegenerative disorders, autism, chemotherapy-induced vomiting, hypertension, migraine headaches, cluster headaches, sexual dysfunction in a mammal (e.g. a human), addictive disorder and withdrawal syndrome, an adjustment disorder, an age-associated learning and mental disorder, anorexia nervosa, apathy, an attention-deficit disorder due to general medical conditions, attention-deficit hyperactivity disorder, behavioral disturbance (including agitation in conditions associated with diminished cognition (e.g., dementia, mental retardation or delirium)), bipolar disorder, bulimia nervosa, chronic fatigue syndrome, conduct disorder, cyclothymic disorder, dysthymic disorder, fibromyalgia and other somatoform disorders, generalized anxiety disorder, an inhalation disorder, an intoxication disorder, movement disorder, (e.g., Huntington's disease or Tardive Dyskinesia), oppositional defiant disorder, peripheral neuropathy, post-traumatic stress disorder, premenstrual dysphoric disorder, a psychotic disorder (brief and long duration disorders, psychotic disorder due to medical condition, psychotic disorder NOS), mood disorder (major depressive or bipolar disorder with psychotic features) seasonal affective disorder, a sleep disorder, a specific developmental disorder, agitation disorder, selective serotonin reuptake inhibition (SSRI) "poop out" syndrome or a Tic disorder (e.g., Tourette's syndrome).

The present invention further provides a method for treating anxiety, depression or stress related disorders comprising administering a therapeutically effective amount of a compound of formula I or II, or a pharmaceutically acceptable salt thereof to the mammal.

The present invention further provides the use of a compound of formula I or II or a pharmaceutically acceptable salt thereof to prepare a medicament for treating or preventing diseases or disorders of the central nervous system.

In another aspect, the invention provides a pharmaceutical composition comprising a therapeutically effective amount of a compound of formula I or II, or a pharmaceutically acceptable salt thereof. The composition may also include a pharmaceutically acceptable carrier.

The present invention further provides a method for treating a disease or condition in a mammal wherein a 5-HT receptor is implicated and modulation of a 5-HT function is desired comprising administering to the mammal a therapeutically effective amount of a compound of formulae I or II, or a pharmaceutically acceptable salt thereof.

The present invention further provides a method for treating a disease or condition in a mammal wherein a 5-HT$_6$ receptor is implicated and modulation of a 5-HT$_6$ function is desired comprising administering to the mammal a therapeutically effective amount of a compound of formula I, described above, or formula II or a pharmaceutically acceptable salt thereof. Wherein formula II is:

II

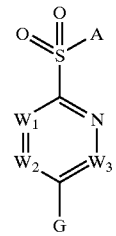

wherein
$W_1$–$W_3$ are —C(R) or N with the proviso that no more than one of $W_1$–$W_3$ are nitrogen;
A is a five- or six-membered monocyclic aromatic ring; a eight- or ten-membered fused aromatic ring system, the five- or six-membered monocyclic aromatic ring and the eight- or ten-membered fused aromatic ring system each optionally containing up to three heteroatoms (O, N, S); or a nine-membered fused aromatic ring system containing one to three heteroatoms (O, N, S), each of the five- or six-membered monocyclic aromatic ring and the eight- to ten-membered fused aromatic ring systems being optionally substituted with 1–4 of R;

Each R is independently selected from H, halo, alkyl, cycloalkyl, substituted alkyl, —OH, alkoxy, substituted alkoxy, —SH, —S-alkyl, —S-substituted alkyl, —CN, —$NO_2$, —$NR_1R_2$, —$NR_1SO_2$-alkyl, —$NR_1SO_2$-aryl, —$COOR_3$, —$CONR_1R_2$, —$SO_2NR_1R_2$, —$SO_2$-alkyl, het, substituted het, aryl and substituted aryl;

G is

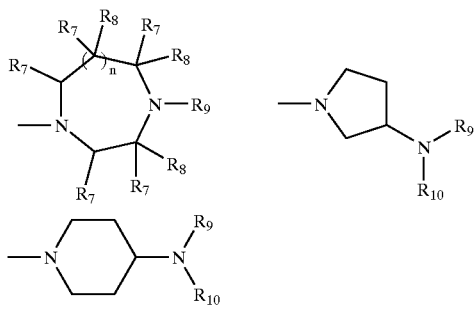

Each $R_1$ and $R_2$ is independently H, alkyl, cycloalkyl, substituted alkyl, aryl, het, substituted aryl, and substituted het, or $R_1$ and $R_2$ when taken together, along with the atom to which they are bound, form a five, six, or seven-membered ring which contains 1–3 heteroatoms selected from N, O, or S;

Each $R_3$ is independently H, alkyl, cycloalkyl, or substituted alkyl;

Each $R_7$ is independently H or alkyl, or oxo provided that $R_8$ is absent when the oxo moiety is bound to the same carbon Each $R_8$ is independently H or alkyl;

Each $R_9$ and $R_{10}$ is independently H, alkyl, or substituted alkyl; and n is 0–1.

Embodiments of the invention may include one or more of the following features. Each R is independently selected from H, F, Cl, Br, I, $C_1$–$C_6$ alkyl, $C_3$–$C_7$ cycloalkyl, $C_1$–$C_3$ alkyl-$C_3$–$C_7$-cycloalkyl, $CF_3$, OH, O—($C_1$–$C_6$-alkyl), O—$C_2$–$C_6$-alkyl-OH, O—$C_2$–$C_6$-$NR_1R_2$, $OCF_3$, SH, S—($C_1$–$C_6$-alkyl) CN, $NO_2$, $NR_1R_2$, $NHSO_2$—$C_1$–$C_4$-alkyl, $COOR_3$, $CONR_1R_2$, $SO_2NR_1R_2$, $SO_2$—$C_1$–$C_4$-alkyl, and aryl optionally substituted with 1 to 3 of H, F, Cl, Br, I, $C_1$–$C_6$-alkyl or -cycloalkyl, OH, O—($C_1$–$C_6$-alkyl), CN, $NR_4R_5$, $CONR_4R_5$, and $SO_2NR_4R_5$. Each $R_1$ and $R_2$ is independently selected from H, $C_1$–$C_4$-alkyl, $C_3$–$C_7$-cycloalkyl, $C_1$–$C_3$-alkyl-$C_3$–$C_7$-cycloalkyl, —$(CH_2)_{0-4}$-aryl, or $R_1$ and $R_2$ when taken together form a five, six, or seven-membered ring which optionally contains a heteroatom selected from N, O, or S. Each $R_3$ is independently selected from H, $C_1$–$C_4$-alkyl, $C_3$–$C_7$-cycloalkyl, and $C_1$–$C_3$-alkyl-$C_3$–$C_7$-cycloalkyl. Each $R_4$ and $R_5$ is independently H, $C_1$–$C_4$-alkyl, $C_3$–$C_7$-cycloalkyl, $C_1$–$C_3$-alkyl-$C_3$–$C_7$-cycloalkyl, or $R_4$ and $R_5$ when taken together form a five, six, or seven-membered ring which optionally contains a heteroatom selected from N, O, or S. Each $R_7$ is H, $C_1$–$C_4$-alkyl, or oxo. Each $R_8$ is H or $C_1$–$C_4$-alkyl. Each $R_9$ and $R_{10}$ is independently selected from H, $C_1$–$C_6$-alkyl, and $C_2$–$C_4$-alkyl-OH. $R_7$–$R_9$ are each H. A is phenyl. The compound is phenyl 5-(1-piperazinyl)-2-pyridinyl sulfone; or 5-(1,4-Diazepan-1-yl)-2-pyridinyl phenyl sulfone; or pharmaceutically acceptable salt thereof. G is

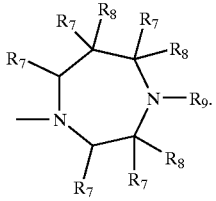

The compounds of formulae I and II also can include isotopic labels. For example the compounds may contain an isotopic label such as at least one atom selected from Carbon-11, Nitrogen-13, Oxygen-15, and Fluorine-18. Isotopically labeled compounds may be used in positron emission tomography, nuclear magnetic resonance imaging and single photon emission tomography.

The present invention further provides isotopically labeled compounds of formulae I or II.

The present invention further provides a method of performing positron emission tomography comprising incorporating an isotopically labeled compound of formulae I or II or a pharmaceutically acceptable salt thereof into tissue of a mammal and detecting the compound incorporated into said tissue.

The present invention further provides a method of performing nuclear magnetic resonance imaging comprising incorporating an isotopically labeled compound of formulae I or II or a pharmaceutically acceptable salt thereof into tissue of a mammal and detecting the compound incorporated in said tissue.

The present invention further provides a method of performing single photon emission computed tomography comprising incorporating an isotopically labeled compound of formulae I or II or a pharmaceutically acceptable salt thereof into tissue of a mammal and detecting the compound incorporated into said tissue.

The invention may also provide novel intermediates and processes for preparing the compounds of the invention.

DETAILED DESCRIPTION OF THE INVENTION

The compounds of the present invention are generally named according to the IUPAC or CAS nomenclature system. Abbreviations which are well known to one of ordinary skill in the art may be used (e.g. "Ph" for phenyl, "Me" for methyl, "Et" for ethyl, "h" for hour or hours, "rt" for room temperature, e.g., 18–25° C., and etc.).

The following definitions are used, unless otherwise described.

The carbon atom content of various hydrocarbon-containing moieties can be indicated by a prefix designating the minimum and maximum number of carbon atoms in the moiety, i.e., the prefix $C_{i\text{-}j}$ indicates a moiety of the integer "i" to the integer "j" carbon atoms, inclusive. Thus, for example, $C_{1\text{-}7}$ alkyl refers to alkyl of one to seven carbon atoms, inclusive.

The term "halo" refers to a halogen atom selected from Cl, Br, I, and F.

The term "alkyl" refers to both straight- and branched-chain moieties. Unless otherwise specifically stated alkyl moieties include between 1 and 10 carbon atoms.

The term "alkenyl" refers to both straight- and branched-chain moieties containing at least one —C═C—. Unless otherwise specifically stated alkenyl moieties include between 1 and 10 carbon atoms.

The term "alkynyl" refers to both straight- and branched-chain moieties containing at least one —C≡C—. Unless otherwise specifically stated alkynyl moieties include between 1 and 10 carbon atoms.

The term "alkoxy" refers to —O-alkyl groups.

The term "cycloalkyl" refers to a cyclic alkyl moiety. Unless otherwise specifically stated cycloalkyl moieties will include between 3 and 7 carbon atoms.

The term "cycloalkenyl" refers to a cyclic alkenyl moiety. Unless otherwise specifically stated cycloalkenyl moieties will include between 3 and 7 carbon atoms and at least one —C═C— group within the cyclic ring.

The term "amino" refers to —NH$_2$.

The term "heterocycloalkyl" refers to a cyclic alkyl moiety including 1–4 heteroatoms in the ring. The heteroatoms are selected from the group consisting of oxygen, sulfur, and nitrogen. Unless otherwise specifically stated heterocycloalkyl moieties include between 5 and 7 ring atoms.

The term "aryl" refers to phenyl and naphthyl.

The term "het" is a C-linked five-(5) membered heteroaryl ring having 1–4 heteroatoms selected from the group consisting of oxygen, sulfur, and nitrogen; a C-linked six (6) membered heteroaryl ring having 1–3 nitrogen atoms; a eight (8) membered bicyclic heteroaryl ring system having 1–3 heteroatoms selected from the group consisting of oxygen, sulfur, and nitrogen; and a ten (10) membered bicyclic heteroaryl ring system having 1–3 heteroatoms selected from the group consisting of oxygen, sulfur, and nitrogen.

Examples of "het" include, but are not limited to, pyridinyl, thiophenyl, furanyl, pyrazolyl, pyrimidinyl, pyridyl, pyridazinyl, imidazolyl, isoxazolyl, pyrazolyl, oxazolyl, oxathiazolyl, oxadiazolyl, thiazolyl, isothiazolyl, thienyl, pyrrolyl, isopyrrolyl, oxathiazolyl-1-oxide, thiadiazolyl, triazolyl, tetrazolyl, thiazolinyl, thiazoledionyl, thiatriazolyl, dithiazolonyl, indoyl, indolinyl, benzofuranyl, benzothiophenyl, benzisoxazolyl, benzimidazoyl, benzoxazolyl, quinolinyl, isoquinolinyl, and quinovalinyl.

The term "substituted alkyl" refers to an alkyl moiety including 1–4 substituents selected from halo, cycloalkyl, cycloalkenyl, heterocycloalkyl, het, aryl, —OQ$_{10}$, —SQ$_{10}$, —S(O)$_2$Q$_{10}$, —S(O)Q$_{10}$, —OS(O)$_2$Q$_{10}$, —C(═NQ$_{10}$)Q$_{10}$, —SC(O)Q$_{10}$, —NQ$_{10}$Q$_{10}$, —C(O)Q$_{10}$, —C(S)Q$_{10}$, —C(O)OQ$_{10}$, —OC(O)Q$_{10}$, —C(O)NQ$_{10}$Q$_{10}$, —C(O)C(Q$_{16}$)$_2$OC(O)Q$_{10}$, —CN, ═O, ═S, —NQ$_{10}$C(O)Q$_{10}$, —NQ$_{10}$C(O)NQ$_{10}$Q$_{10}$, —S(O)$_2$NQ$_{10}$Q$_{10}$, —NQ$_{10}$S(O)$_2$Q$_{10}$, —NQ$_{10}$S(O)Q$_{10}$, and —NO$_2$. Each of the cycloalkyl, heterocycloalkyl, het, aryl, and cycloalkenyl may be optionally substituted with 1–4 substituents independently selected from halo and Q$_{15}$.

The term "substituted aryl" refers to an aryl moiety having 1–3 substituents selected from —OQ$_{10}$, —SQ$_{10}$, —S(O)$_2$Q$_{10}$, —S(O)Q$_{10}$, —OS(O)$_2$Q$_{10}$, —C(═NQ$_{10}$)Q$_{10}$, —SC(O)Q$_{10}$, —NQ$_{10}$Q$_{10}$, —C(O)Q$_{10}$, —C(S)Q$_{10}$, —C(O)OQ$_{10}$, —OC(O)Q$_{10}$, —C(O)NQ$_{10}$Q$_{10}$, —C(O)C(Q$_{16}$)$_2$OC(O)Q$_{10}$, —CN, —NQ$_{10}$C(O)Q$_{10}$, —NQ$_{10}$C(O)NQ$_{10}$Q$_{10}$, —S(O)$_2$NQ$_{10}$Q$_{10}$, —NQ$_{10}$S(O)$_2$Q$_{10}$, —NQ$_{10}$S(O)Q$_{10}$, —NO$_2$, alkyl, substituted alkyl, halo, cycloalkyl, cycloalkenyl, heterocycloalkyl, het, and aryl. The cycloalkyl, cycloalkenyl, heterocycloalkyl, het, and aryl may be optionally substituted with 1–3 substituents selected from halo and Q$_{15}$.

The term "substituted het" refers to a het moiety having 1–3 substituents selected from —OQ$_{10}$, —SQ$_{10}$, —S(O)$_2$Q$_{10}$, —S(O)Q$_{10}$, —OS(O)$_2$Q$_{10}$, —C(═NQ$_{10}$)Q$_{10}$, —SC(O)Q$_{10}$, —NQ$_{10}$Q$_{10}$, —C(O)Q$_{10}$, —C(S)Q$_{10}$, —C(O)OQ$_{10}$, —OC(O)Q$_{10}$, —C(O)NQ$_{10}$Q$_{10}$, —C(O)C(Q$_{16}$)$_2$OC(O)Q$_{10}$, —CN, —NQ$_{10}$C(O)Q$_{10}$, —NQ$_{10}$C(O)NQ$_{10}$Q$_{10}$, —S(O)$_2$NQ$_{10}$Q$_{10}$, —NQ$_{10}$S(O)$_2$Q$_{10}$, —NQ$_{10}$S(O)Q$_{10}$, —NO$_2$, alkyl, substituted alkyl, halo, cycloalkyl, cycloalkenyl, heterocycloalkyl, het, and aryl. The cycloalkyl, cycloalkenyl, heterocycloalkyl, het, and aryl may be optionally substituted with 1–3 substituents selected from halo and Q$_{15}$.

The term "substituted alkenyl" refers to a alkenyl moiety including 1–3 substituents —OQ$_{10}$, —SQ$_{10}$, —S(O)$_2$Q$_{10}$, —S(O)Q$_{10}$, —OS(O)$_2$Q$_{10}$, —C(═NQ$_{10}$)Q$_{10}$, —SC(O)Q$_{10}$, —NQ$_{10}$Q$_{10}$, —C(O)Q$_{10}$, —C(S)Q$_{10}$, —C(O)OQ$_{10}$, —OC(O)Q$_{10}$, —C(O)NQ$_{10}$Q$_{10}$, —C(O)C(Q$_{16}$)$_2$OC(O)Q$_{10}$, —CN, ═O, ═S, —NQ$_{10}$C(O)Q$_{10}$, —NQ$_{10}$C(O)NQ$_{10}$Q$_{10}$, —S(O)$_2$NQ$_{10}$Q$_{10}$, —NQ$_{10}$S(O)$_2$Q$_{10}$, —NQ$_{10}$S(O)Q$_{10}$, —NO$_2$, alkyl, substituted alkyl, halo, cycloalkyl, cycloalkenyl, heterocycloalkyl, het, and aryl. The cycloalkyl, cycloalkenyl, heterocycloalkyl, het, and aryl may be optionally substituted with 1–3 substituents selected from halo and Q$_{15}$.

The term "substituted alkoxy" refers to an alkoxy moiety including 1–3 substituents —OQ$_{10}$, —SQ$_{10}$, —S(O)$_2$Q$_{10}$, —S(O)Q$_{10}$, —OS(O)$_2$Q$_{10}$, —C(═NQ$_{10}$)Q$_{10}$, —SC(O)Q$_{10}$, —NQ$_{10}$Q$_{10}$, —C(O)Q$_{10}$, —C(S)Q$_{10}$, —C(O)OQ$_{10}$, —OC(O)Q$_{10}$, —C(O)NQ$_{10}$Q$_{10}$, —C(O)C(Q$_{16}$)$_2$OC(O)Q$_{10}$, —CN, ═O, ═S, —NQ$_{10}$C(O)Q$_{10}$, —NQ$_{10}$C(O)NQ$_{10}$Q$_{10}$, —S(O)$_2$NQ$_{10}$Q$_{10}$, —NQ$_{10}$S(O)$_2$Q$_{10}$, —NQ$_{10}$S(O)Q$_{10}$, —NO$_2$, alkyl, substituted alkyl, halo, cycloalkyl, heterocycloalkyl, het, aryl, and cycloalkenyl. The cycloalkyl, heterocycloalkyl, het, aryl, and cycloalkenyl may be optionally substituted with 1–3 substituents selected from halo and Q$_{15}$.

The term "substituted cycloalkenyl" refers to a cycloalkenyl moiety including 1–3 substituents —OQ$_{10}$, —SQ$_{10}$, —S(O)$_2$Q$_{10}$, —S(O)Q$_{10}$, —OS(O)$_2$Q$_{10}$, —C(═NQ$_{10}$)Q$_{10}$, —SC(O)Q$_{10}$, —NQ$_{10}$Q$_{10}$, —C(O)Q$_{10}$, —C(S)Q$_{10}$, —C(O)OQ$_{10}$, —OC(O)Q$_{10}$, —C(O)NQ$_{10}$Q$_{10}$, —C(O)C(Q$_{16}$)$_2$OC(O)Q$_{10}$, —CN, ═O, ═S, —NQ$_{10}$C(O)Q$_{10}$, —NQ$_{10}$C(O)NQ$_{10}$Q$_{10}$, —S(O)$_2$NQ$_{10}$Q$_{10}$, —NQ$_{10}$S(O)$_2$Q$_{10}$, —NQ$_{10}$S(O)Q$_{10}$, —NO$_2$, alkyl, substituted alkyl, halo, cycloalkyl, cycloalkenyl, heterocycloalkyl, het, and aryl. The cycloalkyl, cycloalkenyl, heterocycloalkyl, het, and aryl may be optionally substituted with 1–3 substituents selected from halo and Q$_{15}$.

Each Q$_{10}$ is independently selected from —H, alkyl, cycloalkyl, heterocycloalkyl, het, cycloalkenyl, and aryl. The het, heterocycloalkyl, cycloalkyl, cycloalkenyl, and aryl may be optionally substituted with 1–3 substituents selected from halo and Q$_{13}$.

Each Q$_{11}$ is independently selected from —H, halo, alkyl, aryl, and cycloalkyl. The alkyl and cycloalkyl may be optionally substituted with 1–3 substituents independently selected from halo, —NO$_2$, —CN, ═S, ═O, and Q$_{14}$. The aryl may be optionally substituted with 1–3 substituents independently selected from halo, —NO$_2$, —CN, and Q$_{14}$.

Each Q$_{13}$ is independently selected from Q$_{11}$, —OQ$_{11}$, —SQ$_{11}$, —S(O)$_2$Q$_{11}$, —S(O)Q$_{11}$, —OS(O)$_2$Q$_{11}$, —C(═NQ$_{11}$)Q$_{11}$, —SC(O)Q$_{11}$, —NQ$_{11}$Q$_{11}$, —C(O)Q$_{11}$, —C(S)Q$_{11}$, —C(O)OQ$_{11}$, —OC(O)Q$_{11}$, —C(O)NQ$_{11}$Q$_{11}$, —C(O)C(Q$_{16}$)$_2$OC(O)Q$_{10}$, —CN, ═O, ═S, —NQ$_{11}$C(O)Q$_{11}$, —NQ$_{11}$C(O)NQ$_{11}$Q$_{11}$, —S(O)$_2$NQ$_{11}$Q$_{11}$, —NQ$_{11}$S(O)$_2$Q$_{11}$, —NQ$_{11}$S(O)Q$_{11}$, and —NO$_2$, provided that Q$_{13}$ is not ═O or ═S when Q$_{10}$ is aryl or het.

Each $Q_{14}$ is —H or a substituent selected from alkyl, cycloalkyl, cycloalkenyl, phenyl, or naphthyl, each optionally substituted with 1–4 substituents independently selected from —F, —Cl, —Br, —I, —OQ$_{16}$, —SQ$_{16}$, —S(O)$_2$Q$_{16}$, —S(O)Q$_{16}$, —OS(O)$_2$Q$_{16}$, —NQ$_{16}$Q$_{16}$, —C(O)Q$_{16}$, —C(S)Q$_{16}$, —C(O)OQ$_{16}$, —NO$_2$, —C(O)NQ$_{16}$Q$_{16}$, —CN, —NQ$_{16}$C(O)Q$_{16}$, —NQ$_{16}$C(O)NQ$_{16}$Q$_{16}$, —S(O)$_2$NQ$_{16}$Q$_{16}$, and —NQ$_{16}$S(O)$_2$Q$_{16}$. The alkyl, cycloalkyl, and cycloalkenyl may be further substituted with =O or =S.

Each $Q_{15}$ is alkyl, cycloalkyl, cycloalkenyl, phenyl, or naphthyl, each optionally substituted with 1–4 substituents independently selected from —F, —Cl, —Br, —I, —OQ$_{16}$, —SQ$_{16}$, —S(O)$_2$Q$_{16}$, —S(O)Q$_{16}$, —OS(O)$_2$Q$_{16}$, —C(=NQ$_{16}$)Q$_{16}$, —SC(O)Q$_{16}$, —NQ$_{16}$Q$_{16}$, —C(O)Q$_{16}$, —C(S)Q$_{16}$, —C(O)OQ$_{16}$, —OC(O)Q$_{16}$, —C(O)NQ$_{16}$Q$_{16}$, —C(O)C(Q$_{16}$)$_2$OC(O)Q$_{16}$, —CN, —NQ$_{16}$C(O)Q$_{16}$, —NQ$_{16}$C(O)NQ$_{16}$Q$_{16}$, —S(O)$_2$NQ$_{16}$Q$_{16}$, —NQ$_{16}$S(O)$_2$Q$_{16}$, —NQ$_{16}$S(O)Q$_{16}$, and —NO$_2$. The alkyl, cycloalkyl, and cycloalkenyl may be further substituted with =O or =S.

Each $Q_{16}$ is independently selected from —H, alkyl, and cycloalkyl. The alkyl and cycloalkyl may be optionally substituted with 1–3 halos.

Mammal denotes human and animals.

It is to be understood that the present invention encompasses any racemic, optically-active, polymorphic, tautomeric, or stereoisomeric form, or mixture thereof, of a compound of the invention, which possesses the useful properties described herein.

In cases where compounds are sufficiently basic or acidic to form stable nontoxic acid or base salts, administration of the compounds as pharmaceutically acceptable salts may be appropriate. Examples of pharmaceutically acceptable salts which are within the scope of the present invention include organic acid addition salts formed with acids which form a physiological acceptable anion and inorganic salts. Examples of pharmaceutically acceptable salts include, but are not limited to, the following acids acetic, aspartic, benzenesulfonic, benzoic, bicarbonic, bisulfuric, bitartaric, butyric, calcium edetate, camsylic, carbonic, chlorobenzoic, citric, edetic, edisylic, estolic, esyl, esylic, formic, fumaric, gluceptic, gluconic, glutamic, glycollylarsanilic, hexamic, hexylresorcinoic, hydrabamic, hydrobromic, hydrochloric, hydroiodic, hydroxynaphthoic, isethionic, lactic, lactobionic, maleic, malic, malonic, mandelic, methanesulfonic, methylnitric, methylsulfuric, mucic, muconic, napsylic, nitric, oxalic, p-nitromethane-sulfonic, pamoic, pantothenic, phosphoric, monohydrogen phosphoric, dihydrogen phosphoric, phthalic, polygalactouronic, propionic, salicylic, stearic, succinic, sulfamic, sulfanilic, sulfonic, sulfuric, tannic, tartaric, teoclic and toluenesulfonic.

Pharmaceutically acceptable salts may be obtained using standard procedures well known in the art, or example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of this invention may be prepared by the route depicted in Chart A. Commercially available heteroaryl (2) may be used directly or prepared from commercially available hydroxyheteroaryls (1) by treatment with trifluoroacetic anhydride in the presence of base and solvents such as dichloromethane or THF to form heteroaryl (2) as a triflate; alternatively, anilinoheteroaryls 1 may be treated with sodium nitrite and aqueous HCl or HBr to give heteroaryl (2). Heteroaryl (2) is then heated at temperatures ranging from 100–200° C. with thioaryl (3) in the absence of solvent or with solvents such as DMF, N-methylpyrrolidinone, dimethylacetamide, THF, dioxane, acetonitrile, ethyl acetate, dimethoxyethane, ethylene gycol, and ethanol to give arylsulfide (4). Arylsulfide (4) is oxidized to give arylsulfone (5) using oxidants such as hydrogen peroxide in acetic acid or m-chloroperoxybenzoic acid in dichloromethane or other methods such as are taught in March, "Advanced Organic Chemistry: Reactions, Mechanisms, and Structure," McGraw-Hill Book Co., Editions 2–4.

Arylsulfone (5) is then treated with heterocyclic amines (6 or 7) in solvents such as DMF, N-methylpyrrolidinone, dimethylacetamide, THF, dioxane, acetonitrile, ethyl acetate, dimethoxyethane, ethylene gycol, and ethanol with bases such as potassium carbonate, sodium carbonate, cesium carbonate, lithium carbonate, triethylamine, diisopropylethylamine, pyridine or other solvents and bases well known to those versed in the art, at temperatures ranging from 70 to 170° C., to give aminosulfone (8 or 9). Alternatively, arylsulfone (5) and heterocyclic amine (6 or 7) may be reacted in the presence of a catalyst, base, solvent, and temperature as discussed in reviews by Buchwald (Acc. Chem. Res. 1998, 31, 805) and Hartwig (Ang. Chem. Int. Ed. Engl. 1998, 37, 2046) to give 8 or 9.

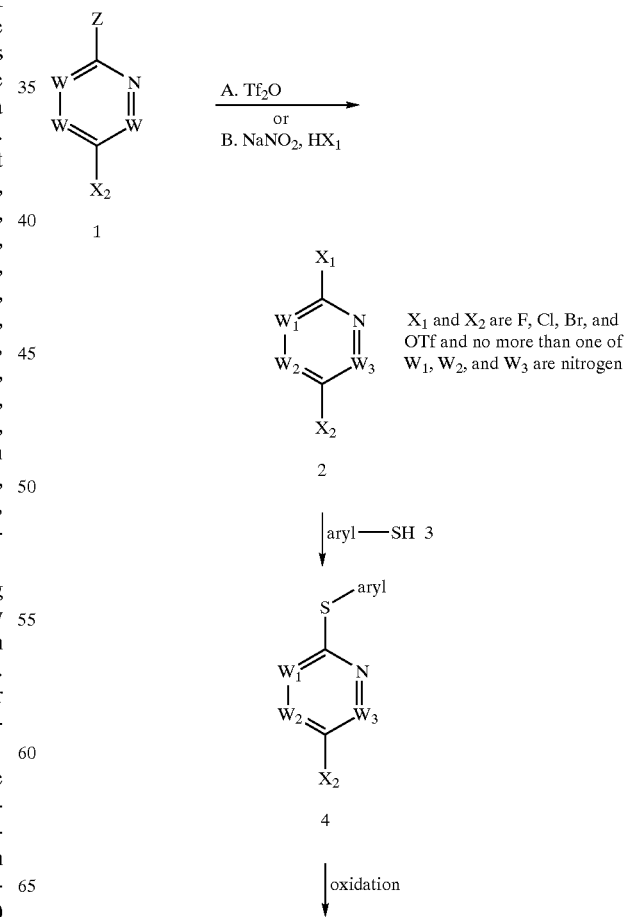

Chart A

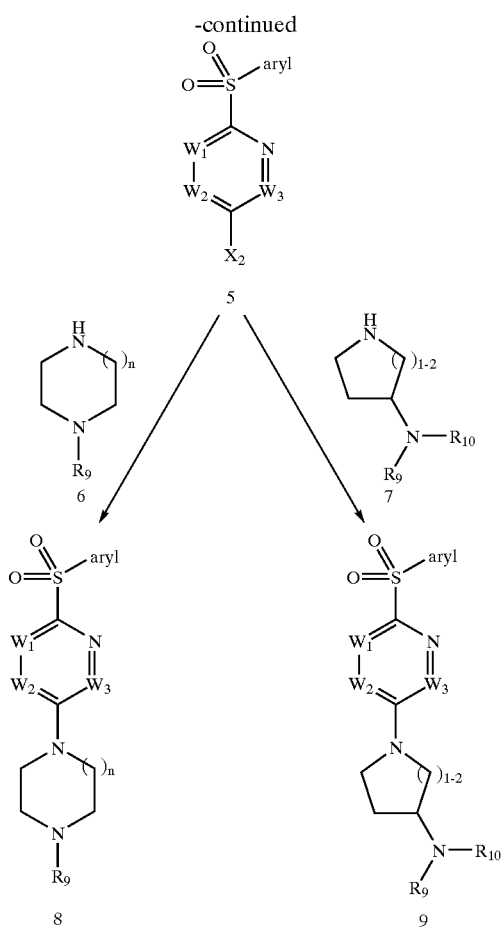

In some embodiments, the compounds are isotopically-labeled compounds. Isotopically-labeled compounds are identical to those recited in Formulae I and II, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine, iodine, and chlorine, such as $^{3}H$, $^{11}C$, $^{14}C$, $^{13}N$, $^{15}O$, $^{18}F$, $^{99m}Tc$, $^{123}I$, and $^{125}I$. Compounds of the present invention and pharmaceutically acceptable salts and prodrugs of said compounds that contain the aforementioned isotopes and/or other isotopes of other atoms are within the scope of the invention. Isotopically-labeled compounds of the present invention are useful in drug and/or substrate tissue distribution and target occupancy assays. For example, isotopically labeled compounds are particularly useful in SPECT (single photon emission computed tomography) and in PET (positron emission tomography).

Single-photon emission computed tomography (SPECT), acquires information on the concentration of isotopically labeled compounds introduced to a mammal's body. SPECT dates from the early 1960's, when the idea of emission traverse section tomography was introduced by D. E. Kuhl and R. Q. Edwards prior to either PET, x-ray CT, or MRI. In general, SPECT requires isotopes that decay by electron capture and/or gamma emission. Example of viable SPECT isotopes include, but are not limited to, 123-iodine ($^{123}I$) and 99m-technetium ($^{99m}Tc$). Subjects are injected with a radioactively labeled agent, typically at tracer doses. The nuclear decay resulting in the emission of a single gamma ray which passes through the tissue and is measured externally with a SPECT camera. The uptake of radioactivity reconstructed by computers as a tomogram shows tissue distribution in cross-sectional images.

Positron emission tomography (PET) is a technique for measuring the concentrations of positron-emitting isotopes within the tissues. Like SPECT, these measurements are, typically, made using PET cameras outside of the living subjects. PET can be broken down into several steps including, but not limited to, synthesizing a compound to include a positron-emitting isotope; administering the isotopically labeled compound to a mammal; and imaging the distribution of the positron activity as a function of time by emission tomography. PET is described, for example, by Alavi et al. in Positron Emission Tomography. published by Alan R. Liss, Inc. in 1985.

Positron-emitting isotopes used in PET include, but are not limited to, Carbon-11, Nitrogen-13, Oxygen-15, and Fluorine-18. In general, positron-emitting isotopes should have short half-lives to help minimize the long term radiation exposure that a patient receives from high dosages required during PET imaging.

In certain instances, PET imaging can be used to measure the binding kinetics of compounds of this invention with 5-HT$_6$ serotonin receptors. For example, administering an isotopically labeled compound of the invention that penetrates into the body and binds to a 5-HT$_6$ serotonin receptor creates a baseline PET signal which can be monitored while administering a second, different, non-isotopically labeled compound. The baseline PET signal will decrease as the non-isotopically labeled compound competes for the binding to the 5-HT$_6$ serotonin receptor.

In general, compounds of formula I that are useful in performing PET or SPECT are those which penetrate the blood-brain barrier, exhibit high selectivity and modest affinity to 5-HT$_6$ serotonin receptors, and are eventually metabolized. Compounds that are non-selective or those that exhibit excessive or small affinity for 5-HT$_6$ serotonin receptors are, generally, not useful in studying brain receptor binding kinetics with respect to 5-HT$_6$ serotonin receptors. Compounds that are not metabolized may harm the patient.

In other embodiments, nuclear magnetic resonance spectroscopy (MRS) imaging can be used to detect the overall concentration of a compound or fragment thereof containing nuclei with a specific spin. In general, the isotopes useful in NMR imaging include, but are not limited to, hydrogen-1, carbon-13, phosphorus-31, and fluorine-19. For instance, compounds containing $^{19}F$ are useful in conducting NMR imaging.

Further, substitution with heavier isotopes such as deuterium, i.e., $^2H$, can afford certain therapeutic advantages resulting from greater metabolic stability, for example increased in vivo half-life or reduced dosage requirements and, hence, maybe preferred in some circumstances. Isotopically labeled compounds of Formula I of this invention can generally be prepared by carrying out the synthetic procedures described above by substituting an isotopically labeled reagent for a non-isotopically labeled reagent.

Compounds of the present invention can conveniently be administered in a pharmaceutical composition containing the compound in combination with a suitable excipient. Such pharmaceutical compositions can be prepared by methods and contain excipients which are well known in the art. A generally recognized compendium of such methods and ingredients is Remington's Pharmaceutical Sciences by E.

W. Martin (Mark Publ. Co., 15th Ed., 1975). The compounds and compositions of the present invention can be administered parenterally (for example, by intravenous, intraperitoneal or intramuscular injection), topically, orally, or rectally.

For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring. The above listing is merely representative and one skilled in the art could envision other binders, excipients, sweetening agents and the like. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices including, but not limited to, those relying on osmotic pressures to obtain a desired release profile (e.g., the OROS drug delivery devices as designed and developed by Alza Corporation).

The compounds or compositions can also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

Pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions can be prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions. Sterilization of the powders may also be accomplished through irradiation and aseptic crystallization methods. The sterilization method selected is the choice of the skilled artisan.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers. Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user. To this extent, the present invention further contemplates the use of the pharmaceutically active materials in personal care compositions such as lotions, cleansers, powders, cosmetics and the like.

The compound is conveniently administered in unit dosage form; for example, containing about 0.05 mg to about 500 mg, conveniently about 0.1 mg to about 250 mg, most conveniently, about 1 mg to about 150 mg of active ingredient per unit dosage form. The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

The compositions can conveniently be administered orally, sublingually, transdermally, or parenterally at dose levels of about 0.01 to about 150 mg/kg, preferably about 0.1 to about 50 mg/kg, and more preferably about 0.1 to about 30 mg/kg of mammal body weight.

For parenteral administration the compounds are presented in aqueous solution in a concentration of from about 0.1 to about 10%, more preferably about 0.1 to about 7%. The solution may contain other ingredients, such as emulsifiers, antioxidants or buffers.

The exact regimen for administration of the compounds and compositions disclosed herein will necessarily be dependent upon the needs of the individual subject being treated, the type of treatment and, of course, the judgment of the attending practitioner.

Generally, compounds of the invention are 5-HT ligands. The ability of a compound of the invention to bind or act at a 5-HT receptor, or to bind or act selectively at a specific 5-HT receptor subtype can be determined using in vitro and in vivo assays that are known in the art. As used herein, the term "bind selectively" means a compound binds at least 2 times, preferably at least 10 times, and more preferably at least 50 times more readily to a given 5-HT subtype than to one or more other subtypes. Preferred compounds of the invention bind selectively to one or more 5-HT receptor subtypes.

The ability of a compound of the invention to act as a 5-HT receptor agonist or antagonist can also be determined using in vitro and in vivo assays that are known in the art. All of the Example compounds provided above are 5-HT ligands, with the ability to displace >50% of a radiolabeled test ligand from one or more 5-HT receptor subtypes at a concentration of 1 μM. The procedures used for testing such displacement are well known and illustrated below.

5-HT$_6$ Receptor Binding Assay
Growth of Cells and Membrane Preparation

Hela cells containing the cloned human 5-HT$_6$ receptor were acquired from Dr. David R. Sibley's laboratory in National Institute of Health (see Sibley, D. R., J. Neurochemistry, 66, 47–56, 1996). Cells were grown in high glucose Dulbecco's modified Eagle's medium, supplemented with L-glutamine, 0.5% sodium pyruvate, 0.3% penicillin-streptomycin, 0.025% G-418 and 5% Gibco fetal bovine serum and then were harvested, when confluent, in cold phosphate buffered saline.

Harvested intact cells were washed once in cold phosphate-buffered saline. The cells were pelleted and resuspended in 100 ml of cold 50 mM Tris, 5 mM EDTA and 5 mM EGTA, pH 7.4. Homogenization was with a Vir Tishear generator, 4 cycles for 30 seconds each at setting 50. The homogenized cells were centrifuged at 700 RPM (1000×g) for 10 minutes and the supernatant was removed. The pellet was resuspended in 100 ml of the above buffer and rehomogenized for 2 cycles. The rehomogenized cells were then centrifuged at 700 RPM (1000×g) for 10 minutes and the supernatant was removed. The combined supernatant (200 ml) was centrifuged at 23,000 RPM (80,000×g) for 1 hour in a Beckman Rotor (42.1 Ti). The membrane pellet was resupended in 50-8-ml of assay buffer containing HEPES 20 mM, MgCl$_2$ 10 mM, NaCl 150 mM, EDTA 1 mM, pH 7.4 and stored frozen in aliqouts at −70° C.

5-HT$_6$ Receptor Binding Assay

The radioligand binding assay used [$^3$H]-lysergic acid diethylamide (LSD). The assay was carried out in Wallac 96-well sample plates by the addition of 11 μl of the test sample at the appropriate dilution (the assay employed 11 serial concentrations of samples run in duplicate), 11 μl of radioligand, and 178 μl of a washed mixture of WGA-coated SPA beads and membranes in binding buffer. The plates were shaken for about 5 minutes and then incubated at room temperature for 1 hour. The plates were then loaded into counting cassettes and counted in a Wallac MicroBeta Trilux scintillation counter.

Binding Constant (Ki) Determination

Binding Constant Determination may be obtained by performing serial dilutions, e.g., eleven dilutions, of test compounds into assay plates using the PE/Cetus Pro/Pette pipetter. These dilutions are followed by radioligand and the bead-membrane mixture prepared as described above. After obtaining the specifically bound cpm, the data are fit to a one-site binding model using GraphPad Prism ver. 2.0. Estimated IC$_{50}$ values are converted to Ki values using the Cheng-Prusoff equation (Cheng, Y. C. et al., Biochem. Pharmacol., 22, 3099–108, 1973).

The compounds and their preparations of the present invention will be better understood in connection with the following examples, which are intended as an illustration of and not a limitation upon the scope of the invention.

EXAMPLES

Preparation of 5-Chloro-2-pyridinyl phenyl sulfide:

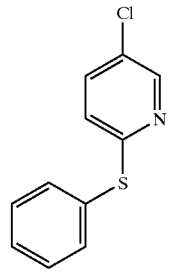

2,5 Dichloropyridine (8.9 g, 60 mmol) and thiophenol (6.1 mL, 60 mmol) were heated to 150° C. for 41 h. The mixture then was removed from heat and cooled to room temperature. Column chromatography (silica gel, 200 mL) using hexanes as eluent gave 8.06 g of the title compound; IR (liq.) 1564, 1548, 1476, 1440, 1356, 1122, 1092, 1024, 1006, 821, 748, 727, 706, 691, 628 cm$^{-1}$. $^1$H NMR (CDCl$_3$) δ 6.8, 7.4, 7.6, 8.38.

Preparation of 5-Chloro-2-pyridinyl phenyl sulfone:

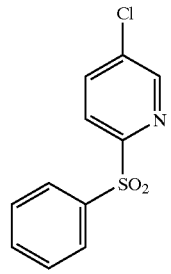

To a mixture of 5-chloro-2-pyridinyl phenyl sulfide (7.54 g, 34 mmol) in glacial acetic acid (30 mL) was added 30% hydrogen peroxide (15 mL, 136 mmol). The mixture was heated at 120° C. for 3.5 h. The mixture then was removed from heat and poured into water (150 mL). A white solid was precipitated, collected by filtration, and washed with water (50 mL). Column chromatography (silica gel, 800 mL) using CH$_2$Cl$_2$ as eluent gave 7.33 g of the title compound; IR (drift) 1327, 1170, 1131, 1119, 1106, 1077, 1010, 846, 782, 764, 758, 716, 689, 626, 618 cm$^{-1}$. $^1$H NMR (CDCl$_3$) δ 7.54, 7.63, 7.87, 8.0, 8.15, 8.6.

Example 1

Phenyl 5-(1-piperazinyl)-2-pyridinyl Sulfone

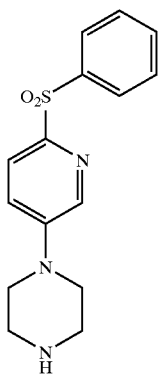

To a mixture of 5-chloro-2-pyridinyl phenyl sulfone (10.2 g, 40.2 mmol) in pyridine (100 mL) was added piperazine (13.8 g, 161 mmol). The mixture was heated to 120° C. in a preheated oil bath for 18 h. The mixture then was removed from heat and cooled to room temperature. The mixture was partitioned between water and ethyl acetate. The layers were separated and the organic layer washed twice with water (2×50 mL). The organic layer was dried with anhydrous magnesium sulfate and concentrated. The solids obtained after concentration were recrystallized from water and dried to give 5.89 g of the title compound; m.p. 126–127° C.; IR (drift) 1568, 1479, 1447, 1306, 1290, 1254, 1175, 1154, 1145, 1104, 830, 756, 715, 688, 602 cm$^{-1}$. $^1$H NMR (CDCl$_3$) δ 3.0, 3.29, 7.13, 7.53, 8.01, 8.26.

Example 2

5-(1,4-Diazepan-1-yl)-2-pyridinyl Phenyl Sulfone Methanesulfonic Acid Salt

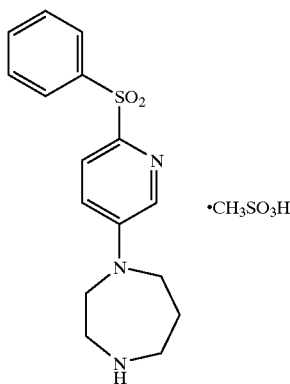

To a mixture of 5-chloro-2-pyridinyl phenyl sulfone (2.0 g, 7.9 mmol) in DMF (50 mL) was added potassium carbonate (2.5 g, 18 mmol) and homopiperazine (1.7 g, 17 mmol). The mixture was heated at 85° C. for 72 h. The mixture then was removed from heat and partitioned between water and ethyl acetate. The layers were separated and the organic layer washed twice with water (2×100 ml). The organic layer was dried over anhydrous magnesium sulfate and concentrated. Column chromatography (silica gel, 75 mL) using 5% CH$_3$OH in CH$_2$Cl$_2$ with 0.7% NH$_4$OH and conversion to the methanesulfonate salt gave 0.182 g of the title compound; IR (drift) 1570, 1304, 1240, 1223, 1207, 1196, 1178, 1145, 1112, 1059, 1052, 785, 715, 688, 645 cm$^{-1}$. $^1$H NMR (DMSO-d$_6$) δ2.0, 3.1, 3.2, 3.38, 3.56, 3.78, 7.26, 7.64, 7.88, 8.21, 8.67.

What is claimed is:

1. A compound of formula I:

wherein $W_1$–$W_3$ are —C(R) or N with the proviso that no more than one of $W_1$–$W_3$ are nitrogen, and further provided that when $W_2$ is N that $W_3$ is not —C(CN);

A is a phenyl or naphthyl ring, a five or six-membered heteroaryl ring, a eight to ten-membered fused heteroaryl ring, the five or six membered monocyclic heteroaryl ring and the eight or ten membered fused heteroaryl ring system each optionally containing up to three heteroatoms (O, N, S); or a nine membered fused heteroaryl ring system containing one to three heteroatoms (O, N, S); each of the five- or six-membered monocyclic heteroaryl ring and the eight- to ten-membered ring systems being optionally substituted with 1–4 of R;

Each R is independently selected from H, halo, alkyl, cycloalkyl, substituted alkyl, —OH, alkoxy, substituted alkoxy, —SH, —S-alkyl, —S-substituted alkyl, —CN, —NO$_2$, —NR$_1$R$_2$, —NR$_1$SO$_2$-alkyl, —NR$_1$SO$_2$-aryl, —COOR$_3$, —CONR$_1$R$_2$, —SO$_2$NR$_1$R$_2$, —SO$_2$-alkyl, het, substituted het, aryl and substituted aryl;

G is

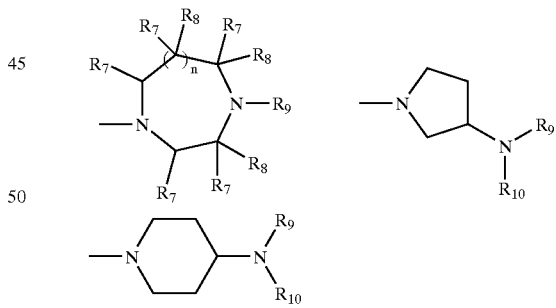

Each $R_1$ and $R_2$ is independently H, alkyl, cycloalkyl, substituted alkyl, aryl, het, substituted aryl, and substituted het, or $R_1$ and $R_2$ when taken together form a five, six, or seven-membered ring which optionally contains a heteroatom selected from N, O, or S;

Each $R_3$ is independently H, alkyl, cycloalkyl, or substituted alkyl;

Each $R_7$ is independently H or alkyl, or oxo provided that $R_8$ is absent when the oxo moiety is bound to the same carbon;

Each $R_8$ is independently H or alkyl;

Each $R_9$ and $R_{10}$ is independently H, alkyl, or substituted alkyl;

wherein cycloalkyl is a cyclic alkyl moiety have between 3 and 7 carbon atoms;

substituted alkyl is an alkyl moiety including 1–4 substituents selected from halo, cycloalkyl, cycloalkenyl, heterocycloalkyl, het, aryl, —$OQ_{10}$, —$SQ_{10}$, —$S(O)_2Q_{10}$, —$S(O)Q_{10}$, —$OS(O)_2Q_{10}$, —$C(=NQ_{10})Q_{10}$, $SC(O)Q_{10}$, —$NQ_{10}Q_{10}$, —$C(O)Q_{10}$, —$C(S)Q_{10}$, —$C(O)OQ_{10}$, —$OC(O)Q_{10}$, —$C(O)NQ_{10}Q_{10}$, —$C(O)C(Q_{16})_2OC(O)Q_{10}$, =CN, =O, =S, —$NQ_{10}C(O)Q_{10}$, $NQ_{10}C(O)NQ_{10}Q_{10}$, —$S(O)_2NQ_{10}Q_{10}$, —$NQ_{10}S(O)_2Q_{10}$, —$NQ_{10}S(O)Q_{10}$, and —NO;

substituted alkoxy is an alkoxy moiety including 1–3 substituents —$OQ_{10}$, —$SQ_{10}$, —$S(O)_2Q_{10}$, —$S(O)Q_{10}$, —$OS(O)_2Q_{10}$, —$C(=NQ_{10})Q_{10}$, —$SC(O)Q_{10}$, —$NQ_{10}Q_{10}$, —$C(O)Q_{10}$, —$C(S)Q_{10}$, —$C(O)OQ_{10}$, —$OC(O)Q_{10}$, —$C(O)NQ_{10}Q_{10}$, —$C(O)C(Q_{16})_2OC(O)Q_{10}$, —CN, =O, =S, —$NQ_{10}C(O)Q_{10}$, —$NQ_{10}C(O)NQ_{10}Q_{10}$, —$S(O)_2NQ_{10}Q_{10}$, —$NQ_{10}S(O)_2Q_{10}$, —$NQ_{10}S(O)Q_{10}$, —$NO_2$, alkyl, substituted alkyl, halo, cycloalkyl, heterocycloalkyl, het, aryl, and cycloalkenyl;

het is a C-linked five-(5) membered heteroaryl ring having 1–4 heteroatoms selected from the group consisting of oxygen, sulfur, and nitrogen; a C-linked six (6) membered heteroaryl ring having 1–3 nitrogen atoms; a eight (8) membered bicyclic heteroaryl ring system having 1–3 heteroatoms selected from the group consisting of oxygen, sulfur, and nitrogen; and a ten (10) membered bicyclic heteroaryl ring system having 1–3 heteroatoms selected from the group consisting of oxygen, sulfur, and nitrogen;

substituted het is a het moiety having 1–3 substituents selected from —$OQ_{10}$, —$SQ_{10}$, —$S(O)_2Q_{10}$, —$S(O)Q_{10}$, —$OS(O)_2Q_{10}$, —$C(=NQ_{10})Q_{10}$, —$SC(O)Q_{10}$, —$NQ_{10}Q_{10}$, —$C(O)Q_{10}$, —$C(S)Q_{10}$, —$C(O)OQ_{10}$, —$OC(O)Q_{10}$, —$C(O)NQ_{10}Q_{10}$, —$C(O)C(Q_{16})_2OC(O)Q_{10}$, —CN, —$NQ_{10}C(O)Q_{10}$, —$NQ_{10}C(O)NQ_{10}Q_{10}$, —$S(O)_2NQ_{10}Q_{10}$, —$NQ_{10}S(O)_2Q_{10}$, $NQ_{10}S(O)Q_{10}$, —$NO_2$, alkyl, substituted alkyl, halo, cycloalkyl, cycloalkenyl, heterocycloalkyl, het, and aryl;

wherein heterocycloalkyl is a cyclic alkyl moiety having between 5 and 7 ring atoms, including 1–4 heteroatoms in the ring selected from the group consisting of oxygen, sulfur and nitrogen;

wherein $Q_{10}$, $Q_{11}$, $Q_{14}$, $Q_{15}$, and $Q_{16}$ are as defined in the specification;

n is 0–1; and any racemic, optically active, tautomeric, stereoisomeric form, mixtures or pharmaceutically acceptable salt thereof.

2. The compound of claim 1, wherein each R is independently selected from H, F, Cl, Br, I, $C_1$–$C_6$ alkyl, $C_3$–$C_7$ Cycloalkyl, $C_1$–$C_3$ alkyl-$C_3$–$C_7$-cycloalkyl, $CF_3$, OH, O—($C_1$–$C_6$-alkyl), O—$C_2$–$C_6$-alkyl-OH, O—$C_2$–$C_6$—$NR_1R_2$, $OCF_3$, SH, S—($C_1$–$C_6$-alkyl) CN, $NO_2$, $NR_1R_2$, $NHSO_2$—$C_1$–$C_4$-alkyl, $COOR_3$, $CONR_1R_2$, $SO_2NR_1R_2$, $SO_2$—$C_1$–$C_4$-alkyl, and aryl optionally substituted with 1 to 3 of H, F, Cl, Br, I, $C_1$–$C_6$-alkyl, $C_1$–$C_6$-cycloalkyl, OH, O—($C_1$–$C_6$-alkyl), CN, $NR_4R_5$, $CONR_4R_5$, and $SO_2NR_4R_5$;

each $R_1$ and $R_2$ is independently selected from H, $C_1$–$C_4$-alkyl, $C_3$–$C_7$-cycloalkyl, $C_1$–$C_3$-alkyl-$C_3$–$C_7$-cycloalkyl, and $(CH_2)_{0-4}$-aryl, or $R_1$ and $R_2$ when taken together form a five, six, or seven-membered ring which optionally contains a heteroatom selected from N, O, or S;

each $R_3$ is independently selected from H, $C_1$–$C_4$-alkyl, $C_3$–$C_7$-cycloalkyl, and $C_1$–$C_3$-alkyl-$C_3$–$C_7$-cycloalkyl;

each $R_4$ and $R_5$ is independently H, $C_1$–$C_4$-alkyl, $C_3$–$C_7$-cycloalkyl, $C_1$–$C_3$-alkyl-$C_3$–$C_7$-cycloalkyl, or $R_4$ and $R_5$ when taken together form a five, six, or seven-membered ring which optionally contains a heteroatom selected from N, O, or S;

each $R_7$ is H, $C_1$–$C_4$-alkyl, or oxo;

each $R_8$ is H or $C_1$–$C_4$-alkyl; and each $R_9$ and $R_{10}$ is independently selected from H, $C_1$–$C_6$-alkyl, and $C_2$–$C_4$-alkyl-OH.

3. A compound of claim 1, wherein A is phenyl.

4. A compound of claim 2, wherein A is phenyl.

5. A compound of claim 1, wherein G is

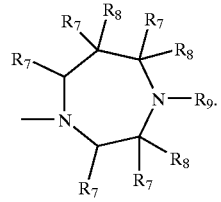

6. A compound of claim 2, wherein G is

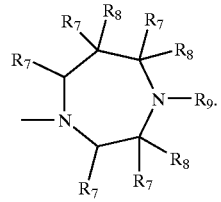

7. A compound of claim 6, phenyl 5-(1-piperazinyl)-2-pyridinyl sulfone or a pharmaceutically acceptable salt thereof.

8. A compound of claim 6, 5-(1,4-diazepan-1-yl)-2-pyridinyl phenyl sulfone or 5-(1,4-diazepan-1-yl)-2-pyridinyl phenyl sulfone methane sulfonic acid salt.

9. A compound of claim 1, wherein the compound includes an isotopic label.

10. A compound of claim 9, wherein the compound includes at least one atom selected from Carbon-11, Nitrogen-13, Oxygen-15 and Fluorine-18.

11. A compound of Formula II, wherein the compound includes an isotopic label.

12. A compound of claim 11, wherein the compound includes at least an atom selected from Carbon-11, Nitrogen-13, Oxygen-15 and Fluorine-18.

13. A pharmaceutical composition comprising a therapeutically effective amount of a compound of formula I:

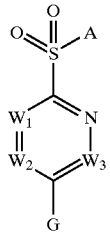

wherein
$W_1$–$W_3$ are —C(R) or N with the proviso that no more than one of $W_1$–$W_3$ are nitrogen, and further provided that when $W_2$ is N that $W_3$ is not —C(CN);

A is a phenyl or naphthyl ring, a five or six-membered heteroaryl ring, a eight to ten-membered fused heteroaryl ring, the five or six membered monocyclic heteroaryl ring and the eight or ten membered fused heteroaryl ring system each optionally containing up to three heteroatoms (O, N, S); or a nine membered fused heteroaryl ring system containing one to three heteroatoms (O, N, S); each of the five- or six-membered monocyclic heteroaryl ring and the eight- to ten-membered ring systems being optionally substituted with 1–4 of R;

Each R is independently selected from H, halo, alkyl, cycloalkyl, substituted alkyl, —OH, alkoxy, substituted alkoxy, —SH, —S-alkyl, —S-substituted alkyl, —CN, —NO$_2$, —NR$_1$R$_2$, —NR$_1$SO$_2$-alkyl, —NR$_1$SO$_2$-aryl, —COOR$_3$, —CONR$_1$R$_2$, —SO$_2$NR$_1$R$_2$, —SO$_2$— alkyl, het, substituted het, aryl and substituted aryl;

G is

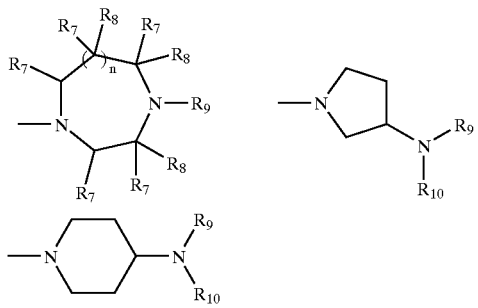

Each $R_1$ and $R_2$ is independently H, alkyl, cycloalkyl, substituted alkyl, aryl, het, substituted aryl, and substituted het, or $R_1$ and $R_2$ when taken together form a five, six, or seven-membered ring which optionally contains a heteroatom selected from N, O, or S;

Each $R_3$ is independently H, alkyl, cycloalkyl, or substituted alkyl;

Each $R_7$ is independently H or alkyl, or oxo provided that $R_8$ is absent when the oxo moiety is bound to the same carbon;

Each $R_8$ is independently H or alkyl;

Each $R_9$ and $R_{10}$ is independently H, alkyl, or substituted alkyl;

wherein
cycloalkyl is a cyclic alkyl moiety have between 3 and 7 carbon atoms;

substituted alkyl is an alkyl moiety including 1–4 substituents selected from halo, cycloalkyl, cycloalkenyl, heterocycloalkyl, het, aryl, —OQ$_{10}$, —SQ$_{10}$, —S(O)$_2$Q$_{10}$, —S(O)Q$_{10}$, —OS(O)$_2$Q$_{10}$, —C(=NQ$_{10}$)Q$_{10}$, SC(O)Q$_{10}$, —NQ$_{10}$Q$_{10}$, —C(O)Q$_{10}$, —C(S)Q$_{10}$, —C(O)OQ$_{10}$, —OC(O)Q$_{10}$, —C(O)NQ$_{10}$Q$_{10}$, —C(O)C(Q$_{16}$)$_2$OC(O)Q$_{10}$, —CN, =O, =S, —NQ$_{10}$C(O)Q$_{10}$, —NQ$_{10}$C(O)NQ$_{10}$Q$_{10}$, —S(O)$_2$NQ$_{10}$Q$_{10}$, —NQ$_{10}$S(O)$_2$Q$_{10}$, —NQ$_{10}$S(O)Q$_{10}$, and —NO;

substituted alkoxy is an alkoxy moiety including 1–3 substituents —OQ$_{10}$, —SQ$_{10}$, —S(O)$_2$Q$_{10}$, —S(O)Q$_{10}$, —OS(O)$_2$Q$_{10}$, —C(=NQ$_{10}$)Q$_{10}$, —SC(O)Q$_{10}$, —NQ$_{10}$Q$_{10}$, —C(O)Q$_{10}$, —C(S)Q$_{10}$, —C(O)OQ$_{10}$, —OC(O)Q$_{10}$, —C(O)NQ$_{10}$Q$_{10}$, —C(O)C(Q$_{16}$)$_2$OC(O)Q$_{10}$, —CN, =O, =S, —NQ$_{10}$C(O)Q$_{10}$, —NQ$_{10}$C(O)NQ$_{10}$Q$_{10}$, —S(O)$_2$NQ$_{10}$Q$_{10}$, —NQ$_{10}$S(O)$_2$Q$_{10}$, —NQ$_{10}$S(O)Q$_{10}$, —NO$_2$, alkyl, substituted alkyl, halo, cycloalkyl, heterocycloalkyl, het, aryl, and cycloalkenyl;

het is a C-linked five-(5) membered heteroaryl ring having 1–4 heteroatoms selected from the group consisting of oxygen, sulfur, and nitrogen; a C-linked six (6) membered heteroaryl ring having a 1–3 nitrogen atoms; a eight (8) membered bicyclic heteroaryl ring system having 1–3 heteroatoms selected from the group consisting of oxygen, sulfur, and nitrogen; and a ten (10) membered bicyclic heteroaryl ring system having 1–3 heteroatoms selected from the group consisting of oxygen, sulfur, and nitrogen;

substituted het is a het moiety having 1–3 substituents selected from —OQ$_{10}$, —SQ$_{10}$, —S(O)$_2$Q$_{10}$, —S(O)Q$_{10}$, —OS(O)$_2$Q$_{10}$, —C(=NQ$_{10}$)Q$_{10}$, —SC(O)Q$_{10}$, —NQ$_{10}$Q$_{10}$, —C(O)Q$_{10}$, —C(S)Q$_{10}$, —C(O)OQ$_{10}$, —OC(O)Q$_{10}$, —C(O)NQ$_{10}$Q$_{10}$, —C(O)C(Q$_{16}$)$_2$OC(O)Q$_{10}$, —CN, —NQ$_{10}$C(O)Q$_{10}$, —NQ$_{10}$C(O)NQ$_{10}$Q$_{10}$, —S(O)$_2$NQ$_{10}$Q$_{10}$, —NQ$_{10}$S(O)$_2$Q$_{10}$, —NQ$_{10}$S(O)Q$_{10}$, —NO$_2$, alkyl, substituted alkyl, halo, cycloalkyl, cycloalkenyl heterocycloalkyl, het, and aryl;

wherein heterocycloalkyl is a cyclic alkyl moiety having between 5 and 7 ring atoms, including 1–4 heteroatoms in the ring selected from the group consisting of oxygen, sulfur and nitrogen;

wherein $Q_{10}$, $Q_{11}$, $Q_{14}$, $Q_{15}$, and $Q_{16}$ are as defined in the specification;

n is 0–1;

any racemic, optically active, tautomeric, stereoisomeric form, mixtures or pharmaceutically acceptable salt thereof; and a pharmaceutically acceptable carrier.

14. The pharmaceutical composition of claim 13, wherein each R is independently selected from H, F, Cl, Br, I, $C_1$–$C_6$ alkyl, $C_3$–$C_7$ cycloalkyl, $C_1$–$C_3$ alkyl-$C_3$–$C_7$-cycloalkyl, CF$_3$, OH, O—($C_1$–$C_6$-alkyl), O—$C_2$–$C_6$-alkyl-OH, O—$C_2$–$C_6$—NR$_1$R$_2$, OCF$_3$, SH, S—($C_1$–$C_6$-alkyl) CN, NO$_2$, NR$_1$R$_2$, NHSO$_2$—$C_2$–$C_4$-alkyl, COOR$_3$, CONR$_3$R$_2$, SO$_2$NR$_1$R$_2$, SO$_2$—$C_1$–$C_4$-alkyl, and aryl optionally substituted with 1 to 3 of H, F, Cl, Br, I, $C_1$–$C_6$-alkyl, $C_1$–$C_6$-cycloalkyl, OH, O—($C_1$–$C_6$-alkyl), CN, NR$_4$R$_5$, CONR$_4$R$_5$, and SO$_2$NR$_4$R$_5$;

each $R_1$ and $R_2$ is independently selected from H, $C_1$–$C_4$-alkyl, $C_3$–$C_7$-cycloalkyl, $C_1$–$C_3$-alkyl-$C_3$–$C_7$-cycloalkyl, and (CH$_2$)$_{0-4}$-aryl, or $R_1$ and $R_2$ when taken together form a five, six, or seven-membered ring which optionally contains a heteroatom selected from N, O, or S;

each $R_3$ is independently selected from H, $C_1$–$C_4$-alkyl, $C_3$–$C_7$-cycloalkyl, and $C_2$–$C_3$-alkyl-$C_3$–$C_7$-cycloalkyl;

each $R_4$ and $R_5$ is independently H, $C_1$–$C_4$-alkyl, $C_3$–$C_7$-cycloalkyl, $C_1$–$C_3$-alkyl-$C_3$–$C_7$-cycloalkyl, or $R_4$ and $R_5$ when taken together form a five, six, or seven-membered ring which optionally contains a heteroatom selected from N, O, or S;

each $R_7$ is H, $C_1$–$C_4$-alkyl, or oxo;

each $R_9$ is H or $C_1$–$C_4$-alkyl;

each $R_9$ and $R_{10}$ is independently selected from H, $C_1$–$C_6$-alkyl, and $C_2$–$C_4$-alkyl-OH; and a pharmaceutically acceptable carrier.

15. The pharmaceutical composition of claim 13, wherein A is phenyl.

16. The pharmaceutical composition of claim 14, wherein A is phenyl.

17. The pharmaceutical composition of claim 13, wherein G is

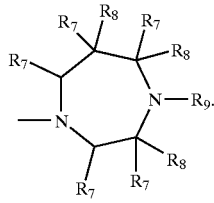

18. A pharmaceutical composition of claim 14, wherein G is

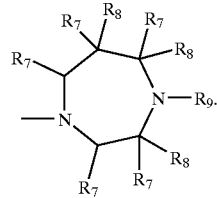

19. A pharmaceutical composition of claim 18, wherein the compound is phenyl 5-(1-piperazinyl)-2-pyridinyl sulfone or a pharmaceutically acceptable salt thereof.

20. A pharmaceutical composition of claim 18, wherein the compound is 5-(1,4-diazepan-1-yl)-2-pyridinyl phenyl sulfone or 5-(1,4-diazepan-1-yl)-2-pyridinyl phenyl sulfone methanesulfonic acid salt.

21. A method for treating a disease or condition in a mammal selected from the group consisting of anxiety, depression or schizophrenia, the method comprising administering to the mammal a therapeutically effective amount of a compound of formula I as defined in claim 1.

22. A method according to claim 21, wherein the compound administered is 5-(1-piperazyl)-2-pyridinyl sulfone or a pharmaceutically acceptable salt thereof.

23. A method according to claim 21, wherein the compound administered is 5-(1,4-diazepan-1-yl)-2-pyridinyl phenyl sulfone or 5-(1,4-diazepan-1-yl)-2-pyridinyl phenyl sulfone methane sulfonic acid salt.

24. A compound of claim 7, wherein the compound includes an isotopic label.

25. A compound of claim 8, wherein the compound includes an isotopic label.

* * * * *